United States Patent [19]
Chou et al.

[11] Patent Number: 5,223,174
[45] Date of Patent: Jun. 29, 1993

[54] MOISTURE-SCAVENGING IMINOALCOHOL-OXAZOLIDINE MIXTURES

[75] Inventors: Chih-Yueh Chou, Elk Grove; Robert E. Malocha, Barrington; Vincent Nocito, Buffalo Grove, all of Ill.

[73] Assignee: Angus Chemical Company, Buffalo Grove, Ill.

[21] Appl. No.: 745,476

[22] Filed: Aug. 15, 1991

[51] Int. Cl.$^5$ .............................................. C09K 3/00
[52] U.S. Cl. .................................................. 252/194
[58] Field of Search ......................... 252/194; 210/698

[56] References Cited

U.S. PATENT DOCUMENTS

| | | | |
|---|---|---|---|
| 3,743,626 | 7/1973 | Emmons | 260/77.5 |
| 3,941,753 | 3/1976 | Brinkmann | 260/77.5 MA |
| 4,115,169 | 9/1978 | Emmons | 156/71 |
| 4,381,388 | 4/1983 | Naples | 528/59 |
| 4,751,257 | 6/1988 | Tominaga | 523/414 |
| 5,126,421 | 6/1992 | Majewski et al. | 528/44 |

FOREIGN PATENT DOCUMENTS

0149765 7/1985 European Pat. Off. .
3019356 11/1981 Fed. Rep. of Germany .
263216 11/1987 Japan .

OTHER PUBLICATIONS

Blomquist et al., "Low VOC Modifiers Improve Urethane Coatings" Modern Paints and Coatings, Apr., 1988, pp. 74-78.
"Experimental Reactive Modifier QM-1007 Technical Data Sheet", Rohm and Haas Co., 1984, pp. 1-13.
Schall, D. "High Solids Isocyanate-Oxazoldine Coatings" Water-Borne— & Higher-Solids Coatings Symposium, 1985, pp. 120-139.
Watson et al. "A Major Advance in Acrylic Urethane Coatings", Rosin Review, vol. 27, No. 4, pp. 12-23.

*Primary Examiner*—Robert L. Stoll
*Assistant Examiner*—Joseph D. Anthony
*Attorney, Agent, or Firm*—Arnold, White & Durkee

[57] ABSTRACT

A moisture-scavenging composition including a mixture of moisture scavenging compounds, wherein the mixture consists of from 0 to 100 mole percent of an iminoalcohol compound:

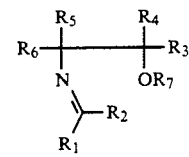

wherein:
$R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group or an aryl group; and from 0 to 100 mole percent of an oxazolidine compound having the structure:

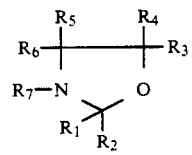

26 Claims, 3 Drawing Sheets

MOISTURE-SCAVENGING IMINOALCOHOL-OXAZOLIDINE MIXTURES

BACKGROUND OF THE INVENTION

1. Field of the Invention

The present invention is generally related to moisture-scavenging compositions, and more particular, the invention is related to moisture-scavenging oxazolidines, ketimine alcohols and aldimine alcohols and mixtures thereof.

2. Background of the Art

Moisture-curable polyurethane coatings are extensively used as commercial and industrial protective and/or decorative coatings. Polyurethane coatings, known in the industry as one of the toughest coatings available, are routinely applied as protective coatings on interior and exterior walls of buildings, industrial machinery, military equipment and vehicles, commercial and passenger vehicles, and any other surface requiring a protective coating. Moisture-curable polyurethane systems are also used extensively as sealants and adhesives.

Moisture-curing polyurethane coating systems include a polyisocyanate component which reacts with atmospheric water at room temperature to form useful films. These systems also include pigments, organic solvents, and a variety of adjuvant components, e.g., surface active agents, dispersants, diluents, and fillers. This type of coating is one of the finest coatings available that can be produced without the application of heat or other external sources of energy. These systems are very useful for objects that cannot be heat-cured such as buildings, large machinery, airplanes, ships and vehicles.

Since the polyisocyanate component reacts with even trace amounts of moisture, extreme care must be taken so that the polyisocyanates do not contact water until they are applied to a surface to be coated. Water is, however, unintentionally and unavoidably introduced into the formulation process in the form of dissolved water in solvents, adsorbed and absorbed water in fillers and pigments, and atmospheric moisture. Subsequent reaction of the water with the polyisocyanate component of the system results in an irreversible reaction which will harden the product, making it unusable before it can be applied to the surface to be coated.

Moisture-curing polyurethane coatings are supplied as both one and two-part systems. In a two-part system, a polyol is chosen that will chemically react with and polymerize the polyisocyanate. The polyol portion generally includes a pigment. The pigmented polyol portion and the polyisocyanate portion are supplied in separate containers to the ultimate user or consumer. The consumer mixes the two portions in accordance with the ratio specified by the manufacturer just prior to use. This admixture has a limited life and must be used within a relatively short period of time or it will polymerize and become unusable in its container.

The two-part system presents several problems to the ultimate user. For example, there is a risk that the pigmented polyol portion and the polyisocyanate portion will not be mixed in the correct ratio. This could seriously detract from the performance of the resulting moisture-cured polyurethane coating. In addition, this approach is expensive in that material is wasted if the entire admixture is not used promptly.

Moisture-curing polyurethane coatings are also supplied as a one-part system eliminating all of the above mentioned problems of the two-part system. In the one-part system, however, extreme care must be taken to assure that all of the moisture is removed from the system prior to packaging the product; otherwise, the polyisocyanate component in the product will react with the available water and polymerize in the container. Sources of water in one-part systems include color pigments and fillers which contain absorbed and adsorbed moisture on their surfaces, water dissolved in solvents, and atmospheric moisture. This waster must be removed in order to produce an acceptable product. The existing methods for preparing color-pigmented moisture-curable polyurethane coatings in a single package require expensive equipment to dry the pigments, solvents, and fillers. In the alternative, moisture-scavenging agents are added to the preparation.

One group of moisture-scavenging compounds are the molecular sieves. Molecular sieves adsorb water into their pores, thereby bonding the water and preventing it from reacting with the polyisocyanate component. An example of a molecular sieve is sodium potassium aluminosilicate, available from the Mobay Corp., Pittsburgh, Pa., under the tradename designation Baylith L Powder. One disadvantage of using molecular sieves is that they reduce the gloss of the cured coating. Another disadvantage of molecular sieves is that they will sometimes plasticize or embrittle the cured coating.

A second group of water-scavenging agents widely used to prevent moisture-contamination of moisture-curable polyurethane coating systems if the monomeric isocyanates. A typical monomeric isocyanate, such as p-toluenesulfonyl isocyanate (Vanchem, Inc. Lockport, Conn.), react with water to generate carbon dioxide and the corresponding sulfonamide, e.g., p-toluenesulfonamide. The carbon dioxide diffuses from the pigment grind during the dehydration phase as carbon dioxide gas.

A disadvantage of monomeric isocyanates is that they are extremely corrosive to skin and toxic. In literature prepared by a supplier of monomeric isocyanates. (Aldrich Chemical Co., Milwaukee, Wis.), monomeric isocyanates are referred to as harmful if swallowed, inhaled, or absorbed through the skin. Moreover, these compounds are listed as extremely corrosive to the tissues of the mucous membranes, upper respiratory tract, and skin. Symptoms of monomeric isocyanate exposure include burning, coughing, nausea and vomiting, chemically induced asthma, chest pain, and pulmonary edema possible causing death. If these compounds are to be handled by the ultimate user, the manufacturer recommends a self-contained breathing apparatus, rubber boots and heavy rubber gloves. Since these compounds are extremely corrosive to skin and toxic, great care must be taken in their manufacture, handling, and use. This enormous health risk dramatically increases the cost of these compounds to the manufacture and the ultimate user.

There is a need for a moisture-scavenger which efficiently, cost effectively, and safely removes water from moisture-curable polyurethane coating systems and from any other application where residual water is a problem, without seriously detracting from the performance of the cured coating.

SUMMARY OF THE INVENTION

In order to satisfy the need for an efficient, cost effective and lower toxicity moisture-scavenger, one aspect of the present invention provides a moisture-scavenging composition including a mixture of moisture scavenging compounds, wherein the mixture consists of from 0 to 100 mole percent of the compound:

(I)

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group, and $R_7$ is a hydrogen atom, a methyl or methylol group, an ethyl or ethylol group, a straight chain or branched chain alkyl or alkanol group, a cycloalkyl group, an acyl group or an aryl group; and from 0 to 100 mole percent of the compound:

(II)

wherein: $R_1$, $R_2$, $R_3$, $R_4$, $R_5$, $R_6$ and $R_7$ are as defined above for compound (I).

In a preferred embodiment, the $R_7$ substituents is a hydrogen atom, a methyl group, an ethyl group, a straight chain or branched chain alkyl group, an acyl group or an aryl group; the $R_{67}$ substituent of the compounds is a hydrogen atom or a methyl group; the $R_5$ substituent of the compounds is a hydrogen atom, a methyl group, an ethyl group or a ($C_3$-$C_5$) branched chain or straight chain alkyl group; the $R_3$ and $R_4$ groups are hydrogen atoms; the $R_1$ substituent is an aryl group, an ethyl group or a ($C_3$-$C_5$) branched or straight chain alkyl group; and the $R_2$ substituent is a hydrogen atom, a methyl group, an ethyl group or a ($C_3$-$C_5$) branched or straight chain alkyl group, or $R_1$ and $R_2$ are fused together with the attached carbon to form a cycloalkane ring.

A further aspect of the invention is directed to a method of dehydrating a preparation. According to the method, an effective amount of the moisture-scavenging composition including at least one of the compounds described above is intimately admixed with the preparation. In one preferred embodiment, the moisture-scavenging compound is at least one of a ketimine or aldimine alcohol of compound (I) and an oxazolidine compound (II) and the effective amount of the composition includes from 1 to 3 moles of the moisture-scavenging compound for every mole of water in the preparation to be dehydrated.

The moisture-scavenging compositions of the invention can consist entirely of the moisture-scavenging compounds described above. In the alternative, the composition can include an effective amount of pigments, organic solvents, fillers, polyisocyanates and adjuvants. The amount of the moisture-scavenging compounds included in the composition is critical to the invention to the extent that the composition must include a sufficient amount of a moisture-scavenging compound to dehydrate the preparation to which it is added to, e.g., an organic solvent, or a pigment millbase preparation. Furthermore, the composition must contain a sufficient amount of the moisture-scavenger compound to prepare anhydrous compositions useful in applications in which water is preferably avoided, e.g., moisture-curable polyurethane applications, or dehydration of surfaces onto which moisture-curable coatings are to be applied.

BRIEF DESCRIPTION OF THE DRAWINGS

FIG. 1 graphically illustrates the relative hydrolysis rates of the 2-(1-hydroxy-2-hydroxymethylbutyl)(cyclohexylidine) amine/4-ethyl-4-hydroxymethyl-1,3-oxazolidine-2-spiro-1'-cyclohexane mixture (—●—), the 2-(1-hydroxybutyl)(1-phenyl-1-ethylidine) amine/4-ethyl-2-methyl-2-phenyl-1,3-oxazolidine mixture (—+—), the 2-(1-hydroxy-2-hydroxymethylbutyl)(1-phenyl-1-ethylidine) amine/4-ethyl-4-hydroxymethyl-2-methyl-2-phenyl- 1,3-oxazolidine mixture (—*—), the 2-(1-hydroxybutyl)(2-heptylidine) amine/4-ethyl-2-methyl-2-pentyl-1,3-oxazolidine mixture (—□—), the 2-(1-hydroxybutyl)(5-methyl-2-hexylidine) amine/4-ethyl-2-methyl-2-(3-methylbutyl)-1,3-oxazolidine mixture (—x—), the 2-(1-hydroxy-2-hydroxymethylbutyl)(5-methyl-2-hexylidine) amine/4-ethyl-4-hydroxymethyl-2-methyl-2-(3-methylbutyl)-1,3-oxazolidine mixture (— —), and the 2-(1-hydroxybutyl)(2,6-dimethyl-4-heptylidine) amine/2,2-(di-2-methylpropyl)-4-ethyl-1,3-oxazolidine mixture (—Δ—);

DESCRIPTION OF THE PREFERRED EMBODIMENT

The present invention provides a moisture-scavenging composition including a new class of moisture-scavenging compounds. The composition can be advantageously used in the formulation of specially moisture-curable polyurethane systems, including sealants, adhesives and coatings, and in any other application in which residual water is a problem. It has been discovered that a class of compounds including ketimine and aldimine alcohols and substituted monocyclic oxazolidines are excellent moisture-scavengers. The prior art has disclosed a rather broad class of oxazolidine compounds as crosslinking reagents, reacting with polyfunctional isocyanates in the presence of polyols or water to form polymeric coatings. U.S. Pat. No. 4,101,527 disclosed an equimolar reaction of an oxazolidine with a polyfunctional isocyanate in the presence of water to form a polyurethane coating. U.S. Pat. No. 3,941,753 describes pre-polymers for coating formation prepared from the reaction of a ketiminoalkanol with a polyisocyanate. Bicyclic moisture scavenging oxazolidine compounds for use in formulating polyurethane coatings are disclosed in copending U.S. patent application Ser. No. 07/624,062 by Chou, et al., entitled "Moisture Scavenging Oxazolidines", filed Dec. 4, 1990.

The moisture-scavenging composition of the present invention includes a mixture of moisture scavenging compounds, wherein the mixture consists of from 0 to 100 mole percent of the compound:

(I)

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group or an aryl group; and from 0 to 100 mole percent of the compound:

(II)

wherein: $R_1$, $R_2$, $R_3$, $R_4$, $R_5$, $R_6$ and $R_7$ are as defined above for compound (I).

Referring to the moisture-scavenging ketimine or aldimine alcohol compounds (I) of the present invention, the preferred R group substituents are those which increase the reactivity of the compound to water. Without limiting the invention, it has been discovered that aliphatic or aromatic R group substituents increase the reactivity of the compound to water. The moisture-scavenging ketimine or aldimine alcohol compounds (I) of the present invention react chemically with water in the following manner:

As shown above, the reaction products are an amino alcohol and a carbonyl compound. One mole of moisture-scavenging ketimine or aldimine alcohol will react with and remove one mole of water. Therefore, it is preferred that the moisture-scavenging compositions of the invention containing ketimine or aldimine alcohols include at least one mole of the moisture-scavenging ketimine or aldimine alcohol for each mole of water to be removed. However, since a perfectly efficient reaction environment cannot be guaranteed in industrial settings, it is preferable that from 1 to about 3 moles of the moisture-scavenging ketimine or aldimine alcohol be included for every mole of water to be removed. Greater amounts of the ketimine or aldimine alcohol can be added, but are not preferred.

All R group substituents which facilitate the reaction of water with the moisture-scavenging ketiminoalkanol and aldiminoalkanol compounds (I) of the present invention are preferred. In one preferred embodiment of the invention, the $R_7$ substituent is a hydrogen atom, a methyl group, an ethyl group, a straight chain or branched chain alkyl group, an acyl group or an aryl group; the $R_6$ substituent of the compound is a hydrogen atom or a methyl group; the $R_5$ substituent of the compound (I) is a hydrogen atom, a methyl or ethyl group, or a ($C_3$–$C_5$) branched chain or straight chain alkyl group; the $R_3$ and $R_4$ groups are hydrogen atoms; the $R_1$ substituent is an aryl group, an ethyl group or a ($C_3$–$C_5$) branched or straight chain alkyl group; and the $R_2$ substituent is a hydrogen atom, a methyl group, an ethyl group, or a ($C_3$–$C_5$) branched or straight chain alkyl group, or $R_1$ and $R_2$ are fused together with the attached carbon to form a cycloalkane ring. More preferably, the $R_1$ substituent is an aryl group, an ethyl group or a ($C_3$–$C_5$) branched or straight chain alkyl group; the $R_2$ and $R_5$ substituents are methyl or ethyl groups, or ($C_3$–$C_5$) branched or straight chain alkyl groups; the $R_7$ substituent is a hydrogen atom, a methyl group, an ethyl group, an acyl group or an aryl group; and the $R_6$, $R_6$ and $R_4$ groups are hydrogen atoms. Most preferably, the $R_1$ substituent is an aryl group or a ($C_3$–$C_5$) branched or straight chain alkyl group; the $R_2$ substituent is a methyl group, an ethyl group, or a ($C_3$–$C_5$) branched or straight chain alkyl group; the $R_5$ group is a methyl group or an ethyl group; and the $R_7$, $R_6$, $R_3$ and $R_4$ groups are hydrogen atoms.

Referring to the moisture-scavenging oxazolidine compounds (II) of the present invention, the preferred R group substituents are those which increase the reactivity of the ring to water. Without limiting the invention, it has been discovered that aliphatic or aromatic R group substituents increase the reactivity of the ring to water. The moisture-scavenging oxazolidine compounds (II) of the present invention react chemically with water in the following manner:

As shown above, the reaction products are an amino alcohol and a carbonyl compound. One mole of moisture-scavenging oxazolidine compound (II) will react with and remove one mole of water. Therefore, it is preferred that the moisture-scavenging compositions of the invention containing oxazolidine compounds include at least one mole of the moisture-scavenging oxazolidine compound for each mole of water to be removed. However, since a perfectly efficient reaction environment cannot be guaranteed in industrial settings, it is preferable that from 1 to about 3 moles of the moisture-scavenging oxazolidine compound be included for every mole of water to be removed. Greater amounts of the oxazolidine compound can be added, but are not preferred.

All R group substituents which facilitate the reaction of water with the moisture-scavenging oxazolidine compounds (II) of the present invention are preferred. In one preferred embodiment of the invention, the $R_7$ substituent of the compound (II) is a hydrogen atom, a methyl group, an ethyl group, a straight chain or branched chain alkyl group, an acyl group or an aryl group; the $R_6$ substituent of the compound is a hydrogen atom or a methyl group; the $R_5$ substituent of the compound is a hydrogen atom, a methyl or ethyl group, or a ($C_3$–$C_5$) branched chain or straight chain alkyl group; the $R_3$ and $R_4$ groups are hydrogen atoms; the $R_1$ substituent is an aryl group, an ethyl group or a ($C_3$–$C_5$) branched or straight chain alkyl group; and the $R_2$ substituent is a hydrogen atom, a methyl group, an ethyl group, or a ($C_3$–$C_5$) branched or straight chain alkyl group, or $R_1$ and $R_2$ are fused together with the attached carbon to form a cycloalkane ring. More preferably, the $R_1$ substituent is an aryl group, an ethyl group or a ($C_3$–$C_5$) branched or straight chain alkyl group; the $R_2$ and $R_5$ substituents are methyl or ethyl groups, or ($C_3$–$C_5$) branched or straight chain alkyl groups, the $R_7$ substituent is a hydrogen atom, a methyl group, an ethyl group, an acyl group or an aryl group; and the $R_6$, $R_3$ and $R_4$ groups are hydrogen atoms. Most preferably, the $R_1$ substituent is an aryl group or a ($C_3$–$C_5$) branched or straight chain alkyl group; the $R_2$ substituent is a methyl group, an ethyl group, or a ($C_3$–$C_5$) branched or straight chain alkyl group; the $R_5$ group is a methyl group or an ethyl group; and the $R_7$, $R_6$, $R_3$ and $R_4$ groups are hydrogen atoms.

The structure of the R substituents in either the ketiminoalkanols, aldiminoalkanols or monocyclic oxazolidines is determined by the selection of the reactant precursor compounds. Reaction of a primary amino alcohol with a carbonyl compound produces an equilibrium mixture of an oxazolidine compound (II) along with its tautomeric iminoalcohol compound (I) as confirmed by IR spectral data. The amount of each compound present in the equilibrium mixture varies depending on the R substituents. Bulky substituents at $R_1$ and $R_2$, as well as substitution at $R_3$ and $R_4$ will generally shift the equilibrium to the iminoalcohol compound (I), although the compounds of the present invention are not limited thereto. In a specific embodiment of the invention, the 2-(1-hydroxybutyl) (4-methyl-2-pentylidine) amine/4-ethyl-2-methyl-2-(2-methylpropyl)-1,3-oxazolidine iminoalcohol-oxazolidine mixture is prepared by reacting D,L-2-amino-1-butanol with methyl isobutyl ketone. Detailed protocols for synthesizing several preferred moisture-scavengers of the present invention are described herein.

A further aspect of the invention is directed to a method of dehydrating a preparation. In one embodiment the preparation includes at least one pigment and at least one organic solvent. According to the method, an effective amount of the composition of the invention including a ketimine or aldimine alcohol and/or a monocyclic oxazolidine moisture-scavenging compound as described above is intimately admixed with the preparation. In a preferred embodiment, the effective amount includes from 1 to about 3 moles of a mixture of a ketimine or aldimine alcohol compound (I) and an oxazolidine compound (II) for every mole of water in the preparation to be dehydrated.

According to one embodiment of the invention, catalysts are added in combination with the moisture-scavenging iminoalcohol-oxazolidine mixtures of the present invention to facilitate the reaction with water. The addition of a preferred catalyst will, in some instances, minimize the amount of the iminoalcohol-oxazolidine mixture required to remove water from a preparation by increasing the efficiency of the reaction. Furthermore, a preferred catalyst will, in certain circumstances, increase the rate at which the moisture-scavenging compounds react with water. Preferred catalysts include the organometallic catalysts, such as dibutyltin laurate, the mineral acid catalysts and the organic acid catalysts, such as acetic acid.

According to another embodiment of the invention, the reaction between the moisture-scavenging compounds and water occurs at temperatures from ambient to about the boiling point of the preparation being dehydrated. Preferably, this range is from about 40 to about 180 degrees Fahrenheit. Increasing the temperature at which the reaction occurs increases the rate and the efficiency of the reaction.

The moisture-scavenging compounds of the present invention are advantageously used in urethane coating, sealant, and adhesive systems to remove moisture during the formulation, packaging and application steps. The present invention provides the producer of specialty polyurethane systems with an expedient and efficient alternative to the physical methods of dehydration, exemplified by molecular sieves and drying machinery, and the potentially toxic prior chemical methods, exemplified by the monomeric isocyanates presently available. The moisture-scavenging compositions of the present invention are further provided for the storage stabilization of moisture-curable polyurethane systems. A still further intended use of the invention is the dehydration of surfaces onto which moisture-curable coatings are to be applied.

The invention provides an anhydrous composition including the moisture-scavenging compounds described above and an organic solvent. Solvents used in the formulation of one and two-component systems are rapidly dehydrated by treating them with the moisture-scavenging composition of the invention. This anhydrous composition is useful in any application where water is preferably avoided, e.g., preparing moisture-curable polyurethane coatings, or dehydrating surfaces prior to applying moisture-curable coatings. The quantity of moisture-scavenger in the composition will vary with the water content of the solvent. The amount of water in the organic solvent being dehydrated can be determined by gas chromatography. The solvents generally used in the formulation of specialty polyurethane systems are compatible with the moisture-scavenging compositions of the present invention. Solvents generally used in the preparation of polyurethane moisture-scavenging preparations include aprotic solvents, such as ketones, esters, ethers, nitroparaffins, glycol esters, glycol ether esters, halogenated hydrocarbons, and alkyl and aromatic hydrocarbons.

Pigments, fillers, polyisocyanates, and adjuvants are suspended in organic solvents. For the purposes of this invention the term "fillers" is intended to include those materials added to a coating preparation to increase the solids content of the coating. The term "adjuvants" is intended to include those materials which are added to the coating formulation to aid application or formation, such as surface active agents, anti-settling agents, diluents, suspending agents and the like. Pigments, fillers, polyisocyanates and adjuvants can also be dehydrated with the water-scavenging compositions of the present invention.

One aspect of the present invention is a substantially anhydrous composition including pigments, fillers, organic solvents, and the moisture-scavenging compounds described above. It has been determined that a reaction period of from 30 minutes to about twenty-four hours is preferred to ensure substantially complete dehydration of pigment preparations. The amount of the moisture-scavenger composition required to dehydrate the pigment or filler will vary with the total water content. Through the addition of the moisture-scavenging composition of the invention, an anhydrous composition is produced including pigments, organic solvent(s), fillers, polyisocyanates and adjuvants. Alternatively, any of the above-listed components can be deleted, depending on the needs of the ultimate user. This anhydrous composition is useful in applications where water is preferably avoided, e.g., in the formulation of moisture-curable polyurethane coatings.

The following examples are presented to describe preferred embodiments and utilities of the present invention and are not meant to limit the present invention unless otherwise stated in the claims appended hereto. Each of the equilibrium mixtures is referred to in the examples by the name of the iminoalcohol compound present in the mixture. These iminoalcohol compounds and their corresponding oxazolidines which form equilibrium mixtures are listed in the table below.

TABLE 1

| Iminoalcohol-Oxazolidine Mixtures of the Present Invention | |
|---|---|
| Iminoalcohol | Oxazolidine |
| 2-(1-hydroxybutyl) (cyclohexylidine) amine | 4-ethyl-1,3-oxazolidine-2-spiro-1'-cyclohexane |
| 2-(1-hydroxy-2-hydroxymethylbutyl) (cyclohexylidine) amine | 4-ethyl-4-hydroxymethyl-1,3-oxazolidine-2-spiro-1'-cyclohexane |
| 2-(1-hydroxybutyl) (4-methyl-2-pentylidine) amine | 4-ethyl-2-methyl-2-(2-methylpropyl)-1,3-oxazolidine |
| 2-(1-hydroxy-2-hydroxymethylbutyl) (4-methyl-2-pentylidine) amine | 4-ethyl-4-hydroxymethyl-2-methyl-2-(2-methylpropyl)-1,3-oxazolidine |
| 2-(1-hydroxybutyl) (1-phenyl-1-ethylidine) amine | 4-ethyl-2-methyl-2-phenyl-1,3-oxazolidine) |
| 2-(1-hydroxy-2-hydroxymethylbutyl) (1-phenyl-1-ethylidine) amine | 4-ethyl-4-hydroxymethyl-2-methyl-2-phenyl-1,3-oxazolidine |
| 2-(1-hydroxybutyl) (2-heptylidine) amine | 4-ethyl-2-methyl-2-pentyl-1,3-oxazolidine |
| 2-(1-hydroxy-2-hydroxymethylbutyl) (2-heptylidine) amine | 4-ethyl-4-hydroxymethyl-2-methyl-2-pentyl-1,3-oxazolidine |
| 2-(1-hydroxybutyl) (5-methyl-2-hexylidine) amine | 4-ethyl-2-methyl-2-(3-methylbutyl)-1,3-oxazolidine |
| 2-(1-hydroxy-2-hydroxymethylbutyl) (5-methyl-2-hexylidine) amine | 4-ethyl-4-hydroxymethyl-2-methyl-2-(3-methylbutyl)-1,3-oxazolidine |
| 2-(1-hydroxybutyl) (2,6-dimethyl-4-heptylidine) amine | 2,2-(di-2-methylpropyl)-4-ethyl-1,3-oxazolidine |
| 2-(1-hydroxy-2-methylpropyl) (4-methyl-2-pentylidine) amine | 2-(2-methylpropyl)-2,4,4-trimethyl-1,3-oxazolidine |
| 2-(1,3-dihydroxy-2-methylpropyl) (4-methyl-2-pentylidine) amine | 4-hydroxymethyl-2,4-dimethyl-2-(2-methylpropyl)-1,3-oxazolidine |

EXAMPLES

Example 1

Preparation of 2-(1-Hydroxybutyl)cyclohexylidine amine/4-Ethyl-1,3-oxazolidine-2-spiro-1'-cyclohexane Mixture D,L-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, cyclohexanone (161.9 grams; 1.6 mol.) was added over a ten minute period resulting in an exothermic reaction (26° C.→65° C.). The reaction mixture was heated to reflux and 24 grams of water were collected in the Dean-Stark trap over a two hour period. The product was purified by vacuum distillation (77°-78° C. @3.5 mm Hg) using a mirrored column (250 mm × 10 mm i.d.) packed with metal helixes. The material was stored udner a nitrogen atmosphere.

Example 2

Preparation of 2-(1-Hydroxy-2-hydroxymethylbutyl)(cyclohexylidine) amine/4-Ethyl-4-hydroxymethyl-1,3-oxazolidine-2-spiro-1'-cyclohexane Mixture 2-Amino-2-ethyl-1,3-propanediol (AEPD®) (178.9 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, cyclohexanone (309.1 grams; 3.1 mol.) was added over a seven minute period causing a lower reaction mixture temperature. The reaction mixture was heated to reflux and 25 grams of water were collected in the dean-Stark trap over a two hour period. The product was purified by vacuum distillation (121° C.–123° C. @2 mm Hg) using a mirrored column (250 mm × 10 mm i.d.) packed with metal helixes. The material was stored under a nitrogen atmosphere.

Example 3

Preparation of 2-(1-Hydroxybutyl)(4-methyl-2-pentylidine) amine/4-Ethyl-2-methyl-2-(2-methylpropyl)-1,3-oxazolidine Mixture D,L-2-Amino-butanol (AB®) (133.7 grams; 1.5 mol.) was added to a 3-neck, 500 ml. round bottom flask equipped with a magnetic stir bar, a 250 ml addition funnel, a thermometer, and a Dean-Stark trap (50 ml capacity). While stirring, 4-methyl-2-pentanone (MIBK) (165.3 grams; 1.6 mol.) was added over a three minute period causing a lower reaction mixture temperature. (20° C.→17° C.). The reaction mixture was heated to reflux and 25 grams of water were collected in the Dean-Stark trap over a six hour period. The crude product was purified by vacuum distillation (91° C. @14 mm Hg) using a mirrored column (250 mm × 10 mm i.d.) packed with metal helixes. The material was stored under a nitrogen atmosphere.

Example 4

Preparation of 2-(1-Hydroxy-2-hydroxymethylbutyl)(4-methyl-2-pentylidine) amine/4-Ethyl-4-hydroxymethyl-2-methyl-2-(2-methylpropyl)-1,3-oxazolidine Mixture 2-Amino-2-ethyl-1,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 4-methyl-2-pentanone (MIBK) (315.7 grams; 3.1 mol.) was added over a three minute period causing the reaction mixture temperature to lower by 1° C. The reaction mixture was heated to reflux and 24 grams of water were collected in the Dean-Stark trap over a fifth-five hour period. The crude product was purified by vacuum distillation (107° C.–109° C. @2 mm Hg) using a mirrored column (250 mm × 10 mm i.d.) packed with metal helixes. The material was stored under a nitrogen atmosphere.

Example 5

Preparation of 2-(1-Hydroxybutyl)(1-phenyl-1-ethylidine) amine/4-Ethyl-2-methyl-2-phenyl-1,3-oxazolidine Mixture D,L-2-Amino-1-butanol (AB®) (133.7 grams; 1.5 mol.) was added to a 3-neck, 500 ml round bottom flask equipped with a magnetic stir bar, a 250 ml. addition funnel, a thermometer, and a Dean-Stark trap (50 ml capacity). While stirring, acetophenone (198.3 grams; 1.6 mol.) was added over a five minute period causing a lower reaction mixture temperature (21° C.→18° C.). The reaction mixture was heated to reflux and 26 grams of water were collected in the Dean-Stark trap over a twenty hour period. The crude product was purified by a vacuum distillation (95°–99° C. @2–3 mm Hg) using a mirrored column (250 mm × 10 mm i.d.) packed with metal helixes. The material was stored under a nitrogen atmosphere.

Example 6

Preparation of 2-(1-Hydroxy-2-hydroxymethylbutyl)(1-phenyl-1-ethylidine) amine/4-Ethyl-4-hydroxymethyl-2-methyl-2-phenyl-1,3-oxazolidine Mixture 2-Amino-2-ethyl-1,3-propanediol (AEPD®) (179.4 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, acetophenone (378.7 grams; 3.1 mol.) was added over an eight minute period causing a three degree lowering in the reaction mixture temperature. The reaction mixture was heated to reflux and 20 grams of water were collected in the Dean-Stark trap over a twenty hour period. The crude product was purified by vacuum distillation (114° C.→120° C. @0.9–1.0 mm Hg) using a mirrored column (250 mm × 10 mm i.d.) packed with metal helixes. The material was stored under a nitrogen atmosphere.

Example 7

Preparation of 2-(1-Hydroxybutyl)(2-heptylidine) amine/4-Ethyl-2-methyl-2-pentyl-1,3-oxazolidine Mixture D,L-2-amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 2-heptanone (MAK) (188.3 grams; 1.6 mol.) was added over a three minute period causing a lowering of the reaction mixture temperature (24° C.→20° C.). The reaction mixture was heated to reflux and 24 grams of water were collected in the Dean-Stark trap over a thirteen hour period. The crude product was purified by vacuum distillation (70°–73° C. @0.8–1.0 mm Hg) using a mirrored column (250 mm × 10 mm i.d.) packed with metal helixes. The material was stored under a nitrogen atmosphere.

Example 8

Preparation of 2-(1-Hydroxy-2-hydroxymethylbutyl)(2-heptylidine) amine/4-Ethyl-4-hydroxymethyl-2-methyl-2-pentyl-1,3-oxazolidine Mixture 2-Amino-2-ethyl-1,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 2-heptanone (MAK) (359.6 grams; 3.1 mol.) was added over a five minute period causing a two degree temperature drop in the reaction mixture temperature (24° C.→22° C.). The reaction mixture was heated to reflux and 26 grams of water were collected in the Dean-Stark trap over a thirteen hour period. The crude product was purified by vacuum distillation (97° C.–98° C. @1.0 mm Hg) using a mirrored column (250 mm × 10 mm i.d.) packed with metal helixes. The material was stored under a nitrogen atmosphere.

Example 9

Preparation of
2-(1-Hydroxybutyl)(5-methyl-2-hexylidene)
amine/4-Ethyl-2-methyl-2-(3-methylbutyl)-1,3-oxazolidine Mixture D,L-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 5-methyl-2-hexanone (MIAK) (188.4 grams; 1.6 mol.) was added over a four minute period causing a four degree lowering of the reaction mixture temperature (22° C.→18° C.). The reaction mixture was heated to reflux and 21 grams of water were collected in the Dean-Stark trap over a twelve hour period. The crude product was purified by vacuum distillation (46°-48° C. @0.3 mm Hg) using a mirrored column (250 mm × 10 mm i.d.) packed with metal helixes. The material was stored under a nitrogen atmosphere.

Example 10

Preparation of
2-(1-Hydroxy-2-hydroxymethylbutyl)(5-methyl-2-hexylidene)
amine/4-Ethyl-4-hydroxymethyl-2-methyl-2-(3-methylbutyl)-1,3-oxazolidine Mixture 2-Amino-2-ethyl-1,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 5-methyl-2-hexanone (MIAK) (360.0 grams; 3.1 mol.) was added over a three minute period causing a one degree temperature drop in the reaction mixture temperature (22° C.→21° C.). The reaction mixture was heated to reflux and 25 grams of water were collected in the Dean-Stark trap over a ten hour period. The crude product was purified by vacuum distillation (98°-99° C. @0.3 mm Hg) using a mirrored column (250 mm × 10 mm i.d.) packed with metal helixes. The material was stored under a nitrogen atmosphere.

Example 11

Preparation of
2-(1-Hydroxybutyl)(2,6-dimethyl-4-heptylidene)
amine/2,2-(Di-2-methylpropyl)-4-ethyl-1,3-oxazolidine Mixture D,L,-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (500 ml capacity). While stirring, 2,6-dimethyl-4-heptanone (DIBK) (234.7 grams; 1.3 mol.) was added over a two minute period causing a three degree lowering of the reaction mixture temperature (24° C.→21° C.). the reaction mixture was heated to reflux and 24 grams of water were collected in the Dean-Stark trap over a twenty hour period. The crude product was purified by vacuum distillation (92°-99° C. @1.5-1.8 mm Hg) using a mirrored column (250 mm × 10 mm i.d.) packed with metal helixes. The material was stored under a nitrogen atmosphere.

Example 12

Preparation of
2-(1-Hydroxy-2-methylpropyl)(4-methyl-2-pentylidine)
amine/2-(2-Methylpropyl)-2,4,4-trimethyl-1,3-oxazolidine Mixture 2-Amino-2-methyl-1-propanol (AMP ™) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). The flask was warmed to 45° C. to melt the AMP. While stirring, 4-methyl-2-pentanone (MIBK) (165.3 grams; 1.6 mol.) was added over a five minute period and the mixture was heated to reflux. After thirty-five hours, 23 grams of water were collected in the Dean-Stark trap. The crude product was purified by vacuum distillation (36° C. @1.1 mm Hg) using a mirrored column (250 mm × 10 mm i.d.) packed with metal helixes. The material was stored under a nitrogen atmosphere.

Example 13

Preparation of
2-(1,3-Dihydroxy-2-methylpropyl)(4-methyl-2-pentylidine)
amine/4-Hydroxymethyl-2,4-dimethyl-2-(2-methylpropyl-1,3-oxazolidine Mixture 2-Amino-2-methyl-1,3-propanediol (AMPD ™) (157.7 grams; 1.5 mol.) was added to a 3-neck, 1 liter round bottom flask equipped with a mechanical stirrer, a 500 ml addition funnel, a thermometer, and a Dean-Stark trap (100 ml capacity). The flask was warmed to 115° C. to melt the AMPD. While stirring, 4-methyl-2-pentanone (MIBK) (180.3 grams; 1.8 mol.) was added gradually over a twenty-two minute period to prevent lowering the temperature and precipitation of the AMPD. The mixture was heated to reflux and after twenty-six hours, 24 grams of water were collected in the Dean-Stark trap. The crude product was purified by vacuum distillation (95° C.-100° C. @1.8-2.0 mm Hg) using a mirrored column 250 mm × 10 mm i.d.) packed with metal helixes. The material was stored under a nitrogen atmosphere.

Example 14

Water Hydrolysis Comparison Study

The appropriate amount of an iminoalcohol-oxazolidine mixture (0.02 mol.) was added to a 100 ml volumetric flask and was diluted with some acetonitrile. Five equivalents of water (0.10 mol., 1.8 grams) and a 10 mole % catalyst load of acetic acid based on the iminoalcohol-oxazolidine mixture (0.002 mol., 0.12 grams) were added to the solution. The solution was then diluted to the mark on the volumetric flask with acetonitrile. The amount of iminoalcohol-oxazolidine mixture, acetic acid and water for each solution that was prepared are listed below in Table 2.

TABLE 2

| Iminoalcohol-oxazolidine Mixture (0.02 Moles) | Iminoalcohol-oxazolidine Mixture (Grams) | HOAc (Grams) | Water (Grams) |
|---|---|---|---|
| 2-(1-Hydroxybutyl) (cyclohexylidine) amine | 3.38 | 0.12 | 1.8 |
| 2-(1-Hydroxy-2-hydroxymethylbutyl) (cyclohexylidine) amine | 3.98 | 0.12 | 1.8 |

TABLE 2-continued

| Iminoalcohol-oxazolidine Mixture (0.02 Moles) | Iminoalcohol-oxazolidine Mixture (Grams) | HOAc (Grams) | Water (Grams) |
|---|---|---|---|
| 2-(1-Hydroxybutyl) (4-methyl-2-pentylidine) amine | 3.42 | 0.12 | 1.8 |
| 2-(1-Hydroxy-2-hydroxymethylbutyl) (4-methyl-2-pentylidine) amine | 4.02 | 0.12 | 1.8 |
| 2-(1-Hydroxybutyl) (1-phenyl-1-ethylidine) amine | 3.82 | 0.12 | 1.8 |
| 2-(1-Hydroxy-2-hydroxymethylbutyl) (1-phenyl-1-ethylidine) amine | 4.42 | 0.12 | 1.8 |
| 2-(1-Hydroxybutyl) (2-heptylidine) amine | 3.70 | 0.12 | 1.8 |
| 2-(1-Hydroxy-2-hydroxymethylbutyl) (2-heptylidine) amine | 4.30 | 0.12 | 1.8 |
| 2-(1-Hydroxybutyl) (5-methyl-2-hexylidine) amine | 3.70 | 0.12 | 1.8 |
| 2-(1-Hydroxy-2-hydroxymethylbutyl) (5-methyl-2-hexylidine) amine | 4.30 | 0.12 | 1.8 |
| 2-(1-Hydroxybutyl) 2,6-dimethyl-4-heptylidine) amine | 4.26 | 0.12 | 1.8 |
| 2-(1-Hydroxy-2-methylpropyl) (4-methyl-2-pentylidine) amine | 3.42 | 0.12 | 1.8 |

After the solution was prepared, samples of the solution were held at 60° C. and monitored by gas chromatography every twenty-four minutes for the iminoalcohol-oxazolidine mixture, amino alcohol and ketone content over an eight hour period. A normalized gas chromatographic area count was determined for the above three components. A potential water scavenger candidate was determined by the decrease in iminoalcohol-oxazolidine mixture content with a corresponding appearance of the amino alcohol and ketone content. A graphical representation of the data is made by plotting the normalized peak areas of iminoalcohol, oxazolidine, amino alcohol, and ketone versus time (minutes).

Figure 1:
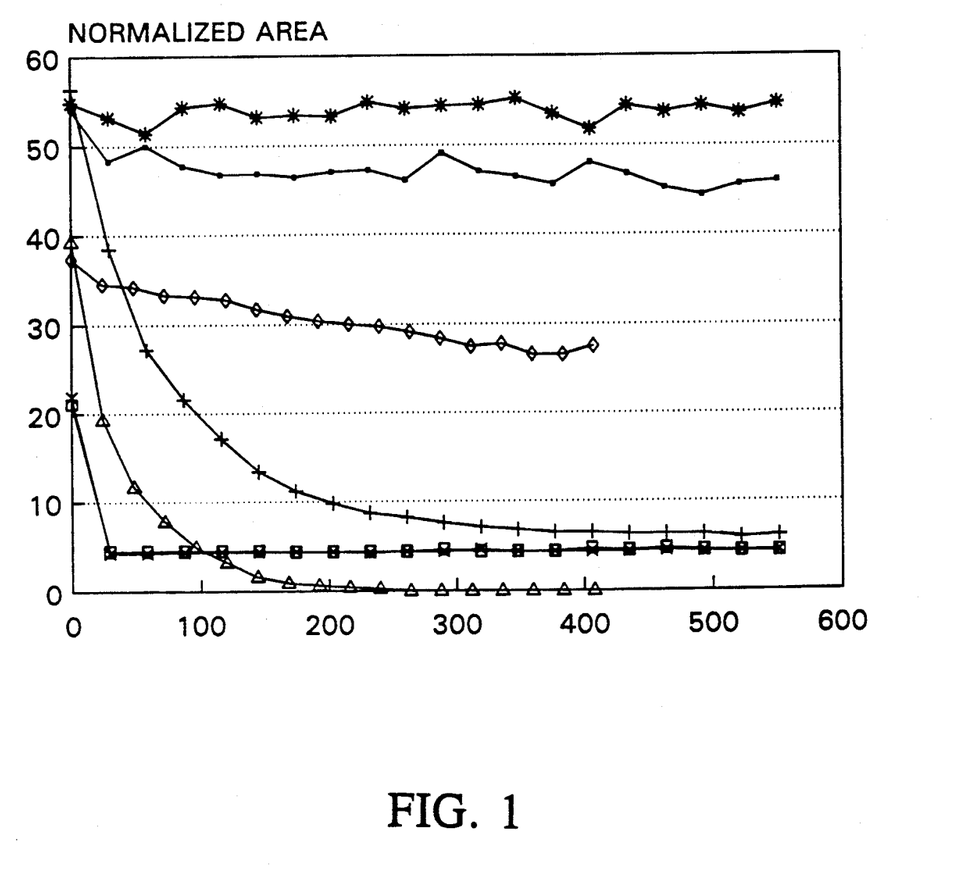
Figure 2:
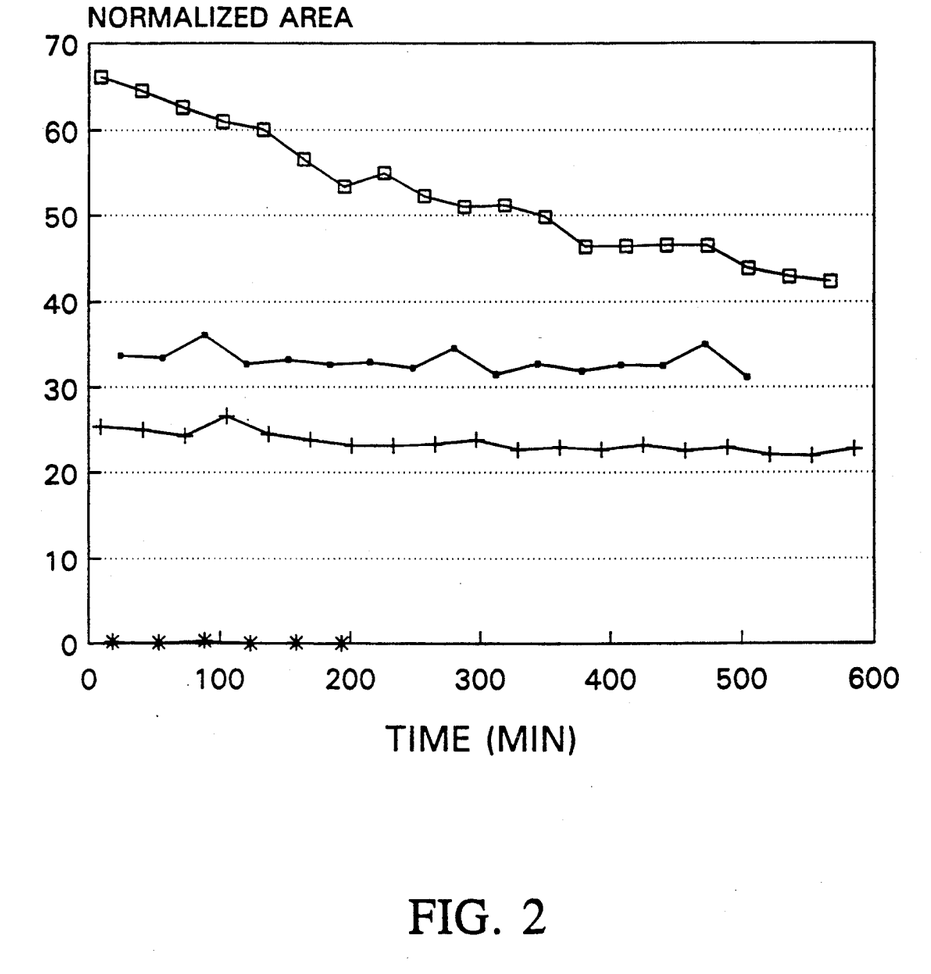
FIG. 2 graphically illustrates the relative hydrolysis rates of the 2-(1-hydroxybutyl)(cyclohexylidine) amine/4-ethyl-1,3-oxazolidine-2-spiro-1'-cyclohexane mixture (—●—), the 2-(1-hydroxybutyl)(4-methyl-2-pentylidine) amine/4-ethyl-2-methyl-2-(2-methylpropyl)-1,3-oxazolidine mixture (—*—), the 2-(1-hydroxy-2-hydroxymethylbutyl)(4-methyl-2-pentylidine) amine/4-ethyl-4-hydroxymethyl-2-methyl-2-(2-methylpropyl)-1,3-oxazolidine mixture (—+—), and the 2-(1-hydroxy-2-hydroxymethylbutyl)(2-heptylidine) amine/4-ethyl-4-hydroxymethyl-2-methyl-2-pentyl-1,3-oxazolidine mixture (—□—)

Relative hydrolysis rates of most of the above listed iminoalcohol-oxazolidine mixtures are compared in FIGS. 1 and 2 which show the normalized peak areas of the oxazolidine versus time. The 2-(1-hydroxybutyl)(4-methyl-2-pentylidine) amine mixture, 2-(1-hydroxybutyl)(2,6-dimethyl-4-heptylidine) amine mixture, 2-(1-hydroxybutyl)(2-heptylidine) amine mixture, 2-(1-phenyl-1-ethylidine) amine mixture are shown to have greater hydrolysis rates that the other iminoalcohol-oxazolidine mixtures which were considered. The iminoalcohol-oxazolidine mixture having the most preferred hydrolysis rate is the 2-(1-hydroxybutyl)(4-methyl-2-pentylidine) amine mixture.

Example 15

Comparison of Water Scavenging Activity

The appropriate amount of an iminoalcohol-oxazolidine mixture (0.02 mol.) was added to a 100 ml volumetric flask and diluted with some acetonitrile. A half an equivalent of water (0.01 mol., 0.18 gram) and a 10 mole % catalyst load of acetic acid (0.002 mol., 0.12 gram) were added to the solution. The solution was then diluted to the mark on the volumetric flask with acetonitrile. The amount of iminoalcohol-oxazolidine mixture, acetic acid and water for each solution that was prepared are listed below in Table 3.

TABLE 3

| Iminoalcohol-oxazolidine Mixture | Iminoalcohol-oxazolidine Mixture (Grams) | HOAc (Grams) | Water (Grams) |
|---|---|---|---|
| 2-(1-Hydroxybutyl)(4-methyl-2-pentylidine) amine | 3.4313 | 0.1229 | 0.1851 |
| 2-(1-Hydroxybutyl)(1-phenyl-1-ethylidine) amine | 3.8276 | 0.1280 | 0.1847 |
| 2-(1-Hydroxybutyl)(2-heptylidine) amine | 3.7129 | 0.1233 | 0.1828 |
| 2-(1-Hydroxybutyl)(5-methyl-2-hexylidine) amine | 3.7109 | 0.1235 | 0.1831 |
| 2-(1-Hydroxybutyl)(2,6-dimethyl-4-heptylidine) amine | 4.2753 | 0.1249 | 0.1822 |
| 2-(1-Hydroxy-2-methylpropyl)(4-methyl-2-pentylidine) amine | 3.4305 | 0.1225 | 0.1850 |

Figure 3:
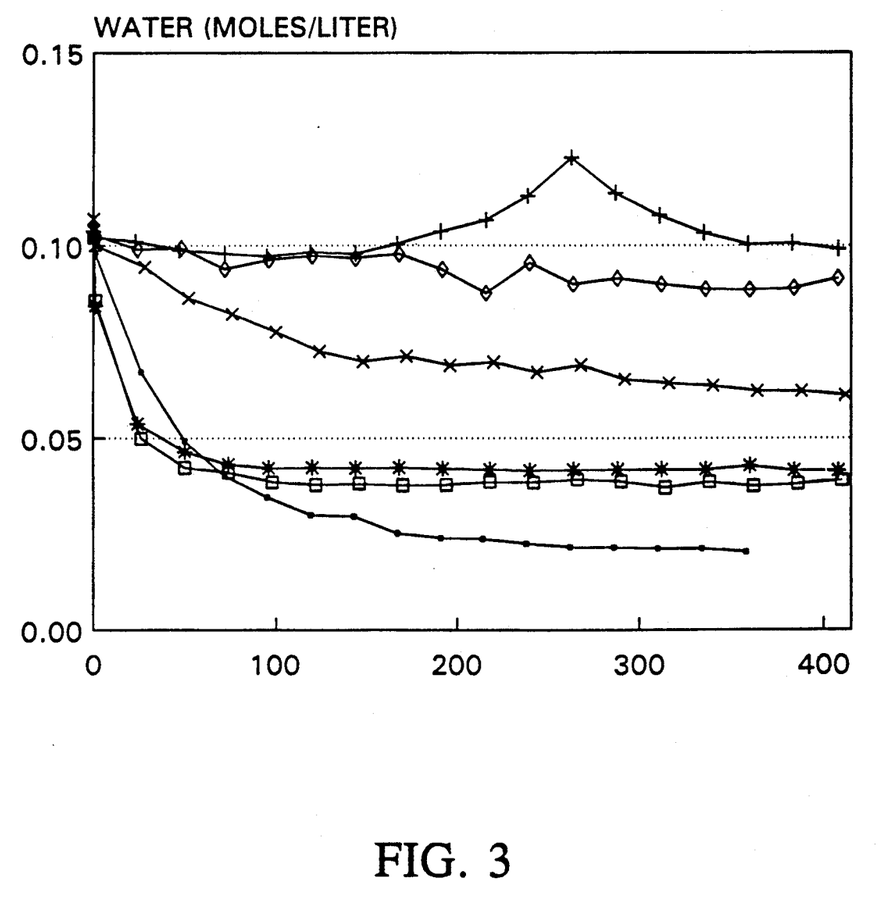
FIG. 3 graphically illustrates the relative water scavenging activity of the 2-(1-hydroxybutyl)(4-methyl-2-pentylidine) amine/4-ethyl-2-methyl-2-(2-methylpropyl)-1,3-oxazolidine mixture (—●—), the 2-(1-hydroxybutyl)(1-phenyl-1-ethylidine) amine/4-ethyl-2-methyl-2-phenyl-1,3-oxazolidine mixture (—+—), the 2-(1-hydroxybutyl)(2-heptylidine) amine/4-ethyl-2-methyl-2-pentyl-1,3-oxazolidine mixture (—*—), the 2-(1-hydroxybutyl)(5-methyl-2-hexylidine) amine/4-ethyl-2-methyl-2-(3-methylbutyl)1,3-oxazolidine mixture (—□—), the 2-(1-hydroxybutyl)(2,6-dimethyl-4-heptylidine) amine/2,2-(di-2-methylpropyl)-4-ethyl-1,3-oxazolidine mixture (—x—), and the 2-(1-hydroxy- 2- methylpropyl)(4-methyl-2-pentylidine) amine/2-(2-methylpropyl)-2,4,4-trimethyl-1,3-oxazolidine mixture (— —).

After the solution was prepared, samples of the solution were held at 25° C. and monitored by gas chromatography for the iminoalcohol, oxazolidine, amino alcohol and ketone and water content over a six hour period. The concentrations (moles/liter) of the above six materials were monitored as a function of time to determine if a particular iminoalcohol-oxazolidine mixture showed water scavenging activity. The relative water scavenging rates are illustrated in FIG. 3 which illustrates the water concentration as a function of time. The 2-(1-hydroxybutyl)(4-methyl-2-pentylidine) amine mixture, 2-(1-hydroxybutyl)(5-methyl-2-hexylidine) amine mixture and 2-(1-hydroxybutyl)(2-heptylidine) amine mixture were shown to be the most effective moisture scavengers.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims. Any R group substituents which increase the reactivity of a moisture scavenging compound of the present invention to water are within the scope of the present invention. For example, alkenyl and alkynl groups may be selected as R group substituents if these groups increase the reactivity of a moisture scavenging compound to water. Likewise, any substituted R groups which increase the reactivity of the moisture-scavenging compounds to water may be included in the compounds of the present invention.

We claim:

1. A moisture-scavenging composition for dehydrating a preparation comprising an organic solvent and at least one mole of a moisture scavenging compound for every mole of water to be dehydrated, the moisture-scavenging compound being selected from the group consisting of:

an iminoalcohol compound having the structure:

an oxazolidine compound having the structure:

a mixture of the iminoalcohol compound and the oxazolidine compound wherein: $R_1$ and $R_2$ are, individually, selected from the group consisting of a methyl or methylol group, an ethyl or ethylol group, and a branched or straight chain alkyl or alkanol group; $R_3$, $R_4$ and $R_5$ are, individually, selected from the group consisting of a hydrogen atom, a methyl or methylol group, an ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, and ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

2. The moisture-scavenging composition of claim 1 wherein the $R_1$ substituent is selected from the group consisting of an ethyl group and a ($C_3$–$C_5$) branched or straight chain alkyl group, and the $R_2$ substituent is selected from the group consisting of a methyl or ethyl group, and a ($C_3$–$C_5$) branched or straight chain alkyl group.

3. The moisture-scavenging composition of claim 2 wherein the $R_3$ and $R_4$ substituents are hydrogen atoms, the $R_5$ substituent is selected from the group consisting of a hydrogen atom, a methyl group, an ethyl group and a ($C_3$–$C_5$) branched or straight chain alkyl group, the $R_6$ substituent is selected from the group consisting of a hydrogen atom and a methyl group, and the $R_7$ substituent is selected from the group consisting of a hydrogen atom, a methyl group, an ethyl group, a straight chain or branched chain alkyl group, an acyl group and an aryl group.

4. The moisture-scavenging composition of claim 1 including from 1 to 3 moles of said moisture scavenging compound for every mole of water in the preparation to be dehydrated.

5. The moisture-scavenging composition of claim 1 wherein the composition further comprises at least one component selected from the group consisting of pigments, fillers, polyisocyanates and adjuvants.

6. The composition of claim 1 wherein $R_1$ is a branched chain alkyl group; $R_2$ is a methyl group; $R_3$, $R_4$, $R_5$ and $R_6$ are hydrogen atoms; and $R_7$ is an ethyl group.

7. The composition of claim 1 wherein $R_1$ is a 3-methylbutyl group; $R_2$ is a methyl group; $R_3$, $R_4$, $R_5$ and $R_7$ are hydrogen atoms; and $R_6$ is an ethyl group.

8. A substantially anhydrous composition for use in preparing a moisture-curable polyurethane coating, adhesive or sealant comprising:
at least one organic solvent; and
at least one mole of a moisture scavenging compound for every mole of water to be dehydrated, the moisture scavenging compound being selected from the group consisting of:
an iminoalcohol compound having the structure:

an oxazolidine compound having the structure:

a mixture of the iminoalcohol compound and the oxazolidine compound wherein: $R_1$ and $R_2$ are, individually, selected from the group consisting of a methyl or methylol group, an ethyl or ethylol group, and a branched or straight chain alkyl or alkanol group; $R_3$, $R_4$ and $R_5$ are, individually, selected from the group consisting of a hydrogen atom, a methyl or methylol group, an ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

9. The composition of claim 8 wherein the composition further includes at least one pigment.

10. The composition of claim 8 including from 1 to 3 moles of said moisture scavenging compound for every mole of water in the coating, adhesive or sealant to be dehydrated.

11. The composition of claim 8 wherein the $R_1$ substituent is selected from the group consisting of an ethyl group and a ($C_3$–$C_5$) branched or straight chain alkyl group, and the $R_2$ substituent is selected from the group consisting of a methyl or ethyl group, and a ($C_3$–$C_5$) branched or straight chain alkyl group.

12. The composition of claim 8 wherein the $R_3$ and $R_4$ substituents are hydrogen atoms, the $R_5$ substituent is selected from the group consisting of a hydrogen atom, a methyl group, an ethyl group and a (C₃–C₅) branched or straight chain alkyl group, the R₆ substituent is selected from the group consisting of a hydrogen atom and a methyl group, and the R₇ substituent is selected from the group consisting of a hydrogen atom, a methyl group, an ethyl group, a straight chain or branched chain alkyl group, an acyl group and an aryl group.

13. The composition of claim 8 wherein R₁ is a branched chain alkyl group; R₂ is a methyl group; R₃, R₄, R₅ and R₆ are hydrogen atoms; and R₇ is an ethyl group.

14. The composition of claim 8 wherein R₁ is a 3-methylbutyl group; R₂ is a methyl group; R₃, R₄, R₅ and R₇ are hydrogen atoms; and R₆ is an ethyl group.

15. A method of dehydrating a preparation including at least one pigment and at least one organic solvent, comprising intimately admixing with the preparation at least one mole of a moisture scavenging compound for every mole of water to be dehydrated, the moisture scavenging compound being selected from the group consisting of:

an iminoalcohol compound having the structure:

an oxazolidine compound having the structure:

a mixture of the iminoalcohol compound and the oxazolidine compound wherein: R₁ and R₂ are, individually, selected from the group consisting of a methyl or methylol group, an ethyl or ethylol group, and a branched or straight chain alkyl or alkanol group; R₃, R₄ and R₅ are, individually, selected from the group consisting of a hydrogen atom, a methyl or methylol group, an ethyl or ethylol group, and a straight chain or branched chain alkyl or alkanol group; R₆ is selected from the group consisting of a hydrogen atom, a methyl group, an ethyl group, and a straight chain or branched chain alkyl group; and R₇ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the cycloalkyl group, an acyl group and an aryl group, and wherein the concentration of the iminoalcohol compound is from 0 to 100 mole percent and the concentration of the oxazolidine compound is from 0 to 100 mole percent.

16. The method of claim 15 including from 1 to 3 moles of said moisture scavenging compound for every mole of water in the preparation to be dehydrated.

17. The method of claim 15 wherein the R₁ substituent is selected from the group consisting of an ethyl group and a (C₃–C₅) branched or straight chain alkyl group, and the R₂ substituent is selected from the group consisting of a methyl or ethyl group, and a (C₃–C₅) branched or straight chain alkyl group.

18. The method of claim 15 wherein the R₃ and R₄ substituents are hydrogen atoms, the R₅ substituent is selected from the group consisting of a hydrogem atom, a methyl group, an ethyl group and a (C₃–C₅) branched or straight chain alkyl group, the R₆ substituent is selected from the group consisting of a hydrogen atom and a methyl group, and the R₇ substituent is selected from the group consisting of a hydrogen atom, a methyl group, an ethyl group, a straight chain or branched chain alkyl group, an acyl group and an aryl group.

19. The method of claim 15 wherein R₁ is a branched chain alkyl group; R₂ is a methyl group, R₃, R₄, R₅ and R₆ are hydrogen atoms; and R₇ is an ethyl group.

20. The method of claim 15 wherein R₁ is a 3-methylbutyl group; R₂ is a methyl group; R₃, R₄, R₅ and R₇ are hydrogen atoms; and R₆ is an ethyl group.

21. A method of dehydrating a surface comprising:
intimately admixing an organic solvent with at least one mole of a moisture scavenging compound for every mole of water to be dehydrated to form a preparation, wherein the moisture scavenging compound is selected from the group consisting of:
an iminoalcohol compound having the structure:

an oxazolidine compound having the structure:

a mixture of the iminoalcohol compound and the oxazolidine compound wherein: R₁ and R₂ are, individually, selected from the group consisting of a methyl or methylol group, an ethyl or ethylol group, and a branched or straight chain alkyl or alkanol group; R₃, R₄ and R₅ are, individually, selected from the group consisting of a hydrogen atom, a methyl or methylol group, an ethyl or ethylol group, and a straight chain or branched chain alkyl or alkanol group; R₆ is selected from the group consisting of a hydrogen atom, a methyl group, an ethyl group, and a straight chain or branched chain alkyl group; and R₇ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent; and
applying the preparation to a surface to dehydrate the surface.

22. The method of claim 21 including from 1 to 3 moles of said moisture scavenging compound for every mole of water on the surface to be dehydrated.

23. The method of claim 21 wherein the $R_1$ substituent is selected from the group consisting of an ethyl group and a ($C_3$-$C_5$) branched or straight chain alkyl group, and the $R_2$ substituent is selected from the group consisting of a methyl or ethyl group, and a ($C_3$-$C_5$) branched or straight chain alkyl group.

24. The method of claim 21 wherein the $R_3$ and $R_4$ substituents are hydrogen atoms, the $R_5$ substituent is selected from the group consisting of a hydrogen atom, a methyl group, an ethyl group and a ($C_3$-$C_5$) branched or straight chain alkyl group, the $R_6$ substituent is selected from the group consisting of a hydrogen atom and a methyl group, and the $R_7$ substituent is selected from the group consisting of a hydrogen atom, a methyl group, an ethyl group, a straight chain or branched chain alkyl group, an acyl group and an aryl group.

25. The method of claim 21 wherein $R_1$ is a branched chain alkyl group, $R_2$ is a methyl group, $R_3$, $R_4$, $R_5$ and $R_6$ are hydrogen atoms; and $R_7$ is an ethyl group.

26. The method of claim 21 wherein $R_1$ is a 3-methylbutyl group; $R_2$ is a methyl group; $R_3$, $R_4$, $R_5$ and $R_7$ are hydrogen atoms; and $R_6$ is an ethyl group.

* * * * *

UNITED STATES PATENT AND TRADEMARK OFFICE
CERTIFICATE OF CORRECTION

PATENT NO. : 5,223,174
DATED : June 29, 1993
INVENTOR(S) : Chou, et al

It is certified that error appears in the above-indentified patent and that said Letters Patent is hereby corrected as shown below:

In FIGs. 1 and 3 below the x-axis please insert --TIME (MIN)--

In Col. 4, line 41 and Col. 5, line 3 replace

"(- -)" with .

Signed and Sealed this

Twentieth Day of December, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,223,174
DATED : June 29, 1993
INVENTOR(S) : Chou et al

It is certified that error appears in the above-indentified patent and that said Letters Patent is hereby corrected as shown below:

In Col. 17, line 13, Col. 18, line 27, Col. 19, line 34 and Col. 20, line 40 replace In Col. 19, line no. 57 please delete "and wherein the concentration of the cycloalkyl group, an acyl group and an aryl group,"

In Col. 17, line 33 replace "and" with --an--.